US011238599B2

(12) United States Patent
Peng et al.

(10) Patent No.: US 11,238,599 B2
(45) Date of Patent: Feb. 1, 2022

(54) REGION-GROWING MOTION TRACKING METHOD BASED ON BAYESIAN INFERENCE AND POLYNOMIAL FITTING

(71) Applicant: SOUTHWEST PETROLEUM UNIVERSITY, Chengdu (CN)

(72) Inventors: Bo Peng, Chengdu (CN); Shuojie Wen, Chengdu (CN); Tianlan Yang, Chengdu (CN); Tingting He, Chengdu (CN); Yang Wang, Chengdu (CN)

(73) Assignee: SOUTHWEST PETROLEUM UNIVERSITY, Chengdu (CN)

( * ) Notice: Subject to any disclaimer, the term of this patent is extended or adjusted under 35 U.S.C. 154(b) by 0 days.

(21) Appl. No.: 17/385,959

(22) Filed: Jul. 27, 2021

(65) Prior Publication Data

US 2021/0358138 A1    Nov. 18, 2021

(30) Foreign Application Priority Data

Jul. 27, 2020    (CN) .......................... 202010730696.9

(51) Int. Cl.
*G06T 7/277* (2017.01)
*G06T 7/187* (2017.01)
(Continued)

(52) U.S. Cl.
CPC .............. *G06T 7/277* (2017.01); *A61B 8/485* (2013.01); *G06T 7/136* (2017.01); *G06T 7/143* (2017.01);
(Continued)

(58) Field of Classification Search
CPC . A61B 8/485; G06T 2207/10132; G06T 7/20; G06T 7/207; G06T 7/215; G06T 7/223; G06T 7/238; G06T 7/277; G06T 7/10; G06T 7/11; G06T 7/136; G06T 7/143; G06T 7/187; G06T 2207/20076
(Continued)

(56) References Cited

PUBLICATIONS

Wang, Yuqi, Jingfeng Jiang, and Timothy J. Hall. "A 3-D region-growing motion-tracking method for ultrasound elasticity imaging." Ultrasound in medicine & biology 44.8 (2018): 1638-1653. (Year: 2018).*

(Continued)

*Primary Examiner* — Geoffrey E Summers

(57) ABSTRACT

The present invention discloses a region-growing motion tracking method based on Bayesian inference and polynomial fitting, including: determining a target region; selecting candidate points; calculating a posterior probability; determining a seed point by judging the seed point according to the maximum posterior probability threshold and the maximum absolute displacement difference; dividing a known-displacement point set (including an interior point (IP) set and a boundary point (BP) set) and an unknown-displacement point set of the target region; selecting an active growing point, with the maximum posterior probability value in the boundary point set; conducting guided search; updating the displacement value; conducting local polynomial fitting; updating the IP set and the BP set; calculating strain elastogram. Compared with a traditional algorithm, the method of the present invention is higher in accuracy, smaller in displacement tracking error, smoother in displacement image and strain elastogram, and higher in clinical application value.

9 Claims, 6 Drawing Sheets

(51) Int. Cl.
    G06T 7/143    (2017.01)
    G06T 7/136    (2017.01)
    A61B 8/08     (2006.01)
(52) U.S. Cl.
    CPC .... *G06T 7/187* (2017.01); *G06T 2207/10132* (2013.01); *G06T 2207/20076* (2013.01)
(58) Field of Classification Search
    USPC .......................................................... 382/128
    See application file for complete search history.

(56) References Cited

PUBLICATIONS

McCormick, Matthew, Nicholas Rubert, and Tomy Varghese. "Bayesian regularization applied to ultrasound strain imaging." IEEE transactions on biomedical engineering 58.6 (2011): 1612-1620. (Year: 2011).*

Ye, Guoliang, et al. "A model-based displacement outlier removal algorithm for ultrasonic temperature estimation." 2008 IEEE Ultrasonics Symposium. IEEE, 2008. (Year: 2008).*

Chen, Hao, and Tomy Varghese. "Noise analysis and improvement of displacement vector estimation from angular displacements." Medical physics 35.5 (2008): 2007-2017. (Year: 2008).*

Jiang, Jingfeng, and Timothy J. Hall. "A fast hybrid algorithm combining regularized motion tracking and predictive search for reducing the occurrence of large displacement errors." IEEE transactions on ultrasonics, ferroelectrics, and frequency control 58.4 (2011): 730-736. (Year: 2011).*

Ultrasound Elastography for Biomedical Applications and Medicine, edited by Ivan Z. Nenadic, et al., John Wiley & Sons, Incorporated, 2019, pp. 35-70. ProQuest Ebook Central, http://ebookcentral.proquest.com/lib/usptl1/detail.action?docID=5568367. (Year: 2019).*

Peng, Bo, et al. "Augmented Region-Growing-Based Motion Tracking Using Bayesian Inference For Quasi-Static Ultrasound Elastography." 2020 IEEE International Conference on Image Processing (ICIP). IEEE, 2020. (Year: 2020).*

Wen, Shuojie, et al. "Augmenting 3D Ultrasound Strain Elastography by combining Bayesian inference with local Polynomial fitting in Region-growing-based Motion Tracking." 2021 IEEE International Conference on Image Processing (ICIP). IEEE, 2021. (Year: 2021).*

* cited by examiner

REGION-GROWING MOTION TRACKING METHOD BASED ON BAYESIAN INFERENCE AND POLYNOMIAL FITTING

BACKGROUND OF THE INVENTION

Technical Field

The present invention relates to a region-growing motion tracking method based on Bayesian inference and polynomial fitting, where the displacement estimation is to incorporate Bayesian inference and local polynomial fitting into the region-growing framework, which belongs to the field of ultrasound elastography.

Description of Prior Art

Quasi-static ultrasound elastography (UE) is a non-invasive in vivo method for evaluating the mechanical properties of biological tissues. The mechanical properties of tissues are usually closely related to their pathological evolution. Its broad clinical application prospects promote major ultrasound vendors (General Electric, Siemens and Philips) to release its software packages around the world.

In ultrasound elastography applications, motion tracking is a crucial step. Ultrasonic strain elastography (USE) for large deformation imposes a unique challenge to motion tracking. In the USE framework, a pair of ultrasound signals is acquired firstly, and then the displacement between these two signals is estimated. The spatial axial strain (in the acoustic beam direction) is estimated and displayed as a gray-scale image, where dark regions correspond to hard tissues and bright regions to soft tissues. In the process of ultrasonic motion tracking, the speed and accuracy of displacement estimation are very important. The commonly used motion tracking algorithms can be roughly divided into three categories: (a) correlation-based, (b) regularized, and (c) optical-flow-based methods. Recently it has been proved that the deep learning neural network model can also be used to reliably track tissue motion in vivo. For correlation-based motion tracking method, the use of correlation alone cannot overcome tracking error between signals (also known as "peak-hopping" error), because ultrasound signals are destroyed or greatly attenuated by noise during the acquisition process. For the regularized motion tracking method, signal correlation/coherence is combined with motion continuity to suppress the incidence of "peak-hopping" errors. In addition, the guided search strategy can be adopted to reduce the "peak-hopping" errors, and the guided search can be performed by the previous displacement estimation of the previous rows or adjacent columns. The guided search strategy also poses the problem that "poor" guidance will cause accumulate displacement estimation errors.

In order to solve this problem, Chen et al. proposed a region-growing strategy which was borrowed from image segmentation. The basic idea of the algorithm is to start motion tracking from the "seed" and transmit the next highest quality position in the queue during the motion tracking process as the algorithm progresses until obtaining the displacement of the entire target region. The problem of "region-growing" is that if the initial seed point is not selected properly, the displacement results obtained by the strategy may be affected.

SUMMARY OF THE INVENTION

The present invention mainly overcomes the deficiencies in the prior art, and proposes a region-growing motion tracking method based on Bayesian inference and polynomial fitting that improves the accuracy and precision of displacement calculation.

The technical solution provided by the present invention to solve the above technical problem is: a region-growing motion tracking method based on Bayesian inference and polynomial fitting, comprising the following steps:

Step 1: determining a seed point: selecting a region of interest (ROI), and then selecting a candidate point set from displacement estimation points in the ROI; calculating posterior probability values of a candidate point in the candidate point set and four neighborhood points, a sum of maximum posterior probability values (MPPS) of these five points, and a maximum absolute displacement difference; judging whether the candidate point in the ROI is a seed point according to a set threshold, the MPPS and the maximum absolute displacement difference;

Step 2: performing guided search, displacement estimation: determining an initial known-displacement point set, an interior point (IP) set and a boundary point (BP) set after the selection of the seed point, selecting a point with the maximum posterior probability value as an active growing point within the determined BP set, then conducting guided search according to a displacement of the active growing point, and determining a neighborhood and a search range for displacement estimation according to a location and the displacement of the active growing point;

Step 3: conducting local polynomial fitting: when the displacement difference between the displacement estimation point and its neighborhood point is higher than the previously set threshold, the local polynomial fitting is carried out with the displacement estimation point as a center, and the local polynomial fitting is carried out using the IP point around the displacement estimation point, and a fitting value is taken as a new displacement estimation value;

Step 4: updating a status of the point to be estimated: adding a new boundary point to the known-displacement point set after displacement estimation and fitting estimation; converting initial unknown-displacement points into known-displacement points in the neighborhood point set of the active growing points, and update the BP set of the known-displacement point set to generate a new BP set; converting the active growing points from members of the BP set to members of the IP set after estimation, and repeating the above steps until all members of the unknown-displacement point set are converted to the members of known-displacement point set;

Step 5: calculating strain elastogram: obtaining an ultrasonic strain elastic image through a differential calculation of displacement field of ultrasonic elastic motion.[0011] A further technical solution is that the calculation of the posterior probability value is as follows:

A. Calculate the prior probability based on the block matching cross-correlation information;
B. Calculate the likelihood function;
C. Calculate the posterior probability according to the prior probability and likelihood function;

$$Pr(U_x \mid U_{N_x}) = \frac{Pr(U_{N_x} \mid U_x) Pr(U_x)}{Pr(U_{N_x})}; \quad (1)$$

$$Pr(U_{N_x} \mid U_x) = \prod_{x' \in N_x} Pr(U_{x'} \mid U_x); \quad (2)$$

$$Pr(U_{x'} \mid U_x) \propto \max_{V_{x'}} \left[ Pr(V_{x'}) \exp\left( \frac{-\|V_{x'} - U_x\|^2}{2\sigma_u^2} \right) \right]. \quad (3)$$

Where, x represents a position of the current matching block, $U_x$ presents a displacement of the current matching block at the position x, and $Pr(U_x)$ is a prior probability value of $U_x$, x' represents positions of four neighboring matching blocks adjacent to the current matching block, $U_{x'}$ represents a displacement of one of the four neighboring matching blocks, $\{Ux':X' \in N_x\}$; $V_{x'}$ represents a candidate displacement of one of the four neighboring matching blocks, and $Pr(V_{x'})$ is a prior probability value of $V_{x'}$; $U_{Nx}$ represents the displacements of the four neighboring matching blocks, and $Pr(U_{Nx})$ represents a prior probability value of $U_{Nx}$; $Pr(U_{Nx}/U_x)$ is the likelihood function; $Pr(U_{x'}|U_x)$ is the probability value that when the displacement of the current matching block at xposition is $U_x$ and the displacement of the neighboring matching block at x'position is $U_{x'}$; $\|V_{x'}-U_x\|^2$ is a distance between these two points x and x', where a value of $\sigma_u$ is taken as empirical value.[0019] D. Calculate the sum of the maximum posterior probability value (MPPS) according to the following formula;

$$MPPS = \Sigma^{m=1}_{m=-1} \Sigma^{n=1}_{n=-1} \max Pr(u+m, v+n) \ m=0 \text{ or } n=0 \quad (4)$$

Where, u and v are the positions of the candidate points, Pr is the posterior probability value of the point, and the formula execution condition (M=0 or n=0) restricts the accumulation process to be the central candidate point and its four neighborhoods.

A further technical solution is that the block matching cross-correlation information of candidate point is obtained by a similarity measurement method.

A further technical solution is that the calculation of likelihood function is expressed by the probability density of the neighborhood value.

A further technical solution is that the calculation of the prior probability is as follows: the similarity measurement image is converted to probability density image; the region corresponding to the maximum value of the cross-correlation matching is the region with the greatest similarity; the probability value should be greater than or equal to zero, so all the values of similarity measurement should be positive; the values of the similarity measurement are normalized.

A further technical solution is that the basis for the seed point judgment in Step 1 is whether the sum of the maximum posterior probability of the candidate point and the neighboring point is greater than the set threshold and whether the maximum absolute displacement difference is less than the set threshold.

A further technical solution is that the specific process of determining the initial known-displacement point set, IP set and BP set in Step 2 is as follows: all initial seeds are placed in a known-displacement point set, and the rest ROIs are named unknown-displacement point set; in the known-displacement point set, the points in the IP set are all points whose neighborhoods are in the known-displacement point set, and the rest known-displacement points are the boundary points.

A further technical solution is that the step of local polynomial fitting in Step 3 is as follows: the displacement of the point to be estimated is fitted according to the displacement of the known-displacement IP set around the point to be estimated, and then the fitted value is worked out; when the error of the fitted value is less than the error of the estimated value, the fitted value will displace the estimated displacement value of the neighborhood.

A further technical solution is that the local polynomial fitting formula in Step 3 is as follows:

$$f(x, y) = a_0 + a_1 x^2 + a_2 y^2 + a_3 xy + a_4 x + a_5 y; \quad (5)$$

$$R^2 = \sum_{i=1}^{N} [g(x, y) - (a_0 + a_1 x^2 + a_2 y^2 + a_3 xy + a_4 x + a_5 y)]^2. \quad (6)$$

Where, (x, y) are coordinates of one displacement point; N represents a total number of displacement points used for calculating the local polynomial fitting formula; $a_0$, $a_1$, $a_2$, $a_3$, $a_4$, $a_5$ are coefficients of the local polynomial fitting formula to be solved; i represent a serial number; g(x,y) is a known displacement, and $R^2$ is a sum of squared errors; wherein N estimated neighboring displacement points are selected, assuming that a distribution of these N estimated neighboring displacement points satisfies the formula (5); a least square method is adopted to solve the coefficients $a_0$, $a_1$, $a_2$, $a_3$, $a_4$, $a_5$, and then the formula (6) is obtained.

The present invention has the following beneficial effects:

(1) Compared with the traditional algorithm, the method of the present invention is higher in accuracy, smaller in tracking error of axial displacement and strain elastogram, and higher in clinical application value;

(2) Compared with the traditional algorithm, the method of the invention is better in the capability to overcome signal decorrelation and higher in calculation accuracy;

(3) The results of in vivo ultrasound data show that the modulus image reconstructed by the displacement obtained by the region-growing motion tracking method of the present invention is better visualized.

DETAILED DESCRIPTION OF THE PREFERRED EMBODIMENTS

Figure 1:
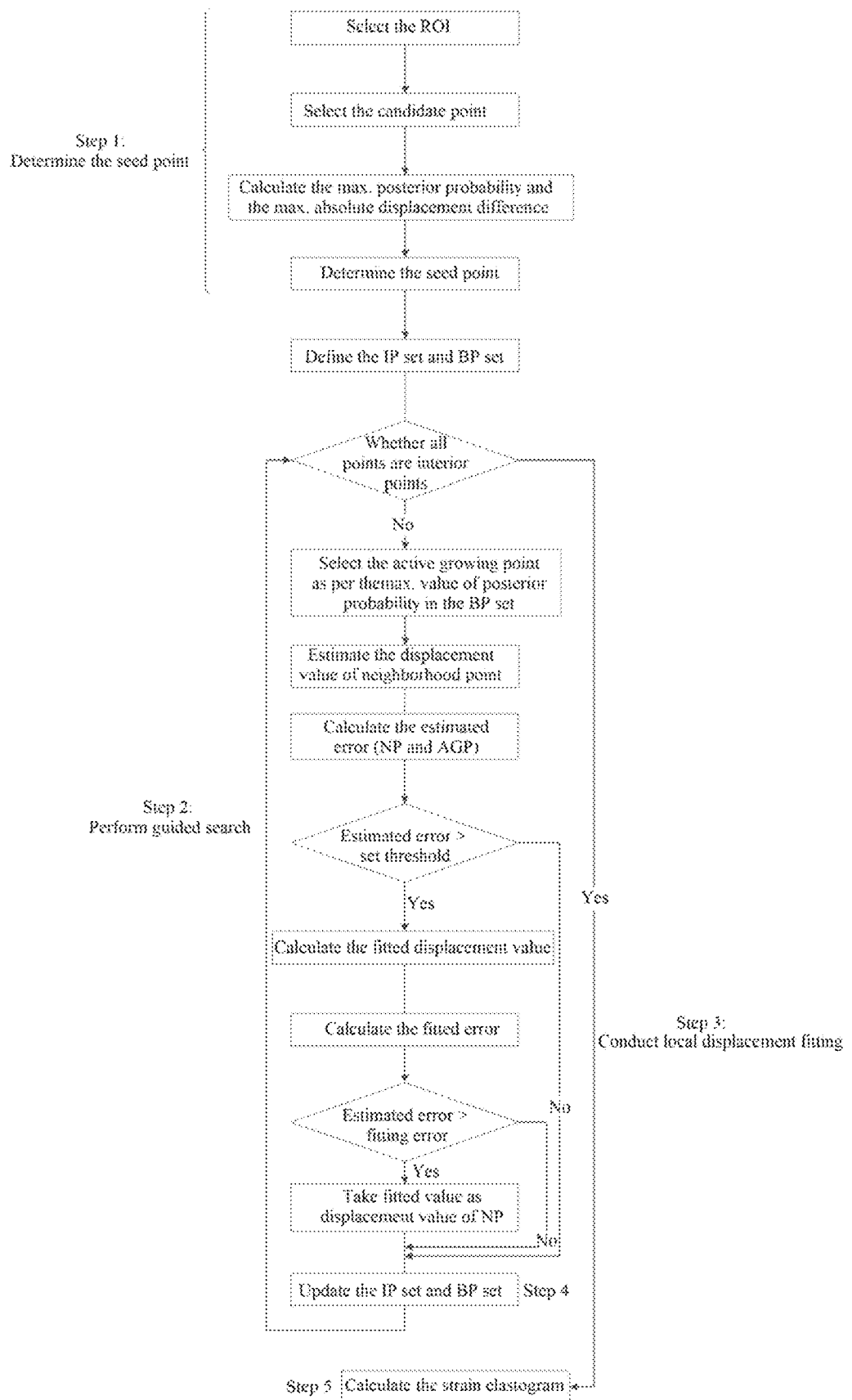
FIG. 1 is a flowchart of the present invention.

The present invention will be further described with the following embodiments and figures;

As shown in FIG. 1, the region-growing motion tracking method based on Bayesian inference and polynomial fitting of the present invention comprises the following steps:

Step 10: Determine the seed point:
Step 11: Select a region of interest (ROI) and determine the axial and lateral size of the displacement estimation region; the ROI usually contains a variety of tissues with different elastic moduli.
Step 12: Determine candidate points, and select a candidate point set from the estimated displacement points of the ROI; the selection method is usually a linear grid of a certain proportion, and the grid can be divided into different proportions based on the data.

Step 13: Calculate the posterior probability value, specifically calculate the maximum posterior probability value of all the points in the candidate point set and calculate the sum of maximum posterior probability values (MPPS) of five points.

Bayesian inference is used to calculate the posterior probability value; the posterior probability calculation is based on the block matching idea of cross-correlation method and the cross-correlation information of adjacent positions around the point to be estimated, that is, calculate the prior probability according to the cross-correlation information of block matching; calculate the likelihood function (expressed by the probability density of the neighborhood value); calculate the posterior probability value according to the prior probability and the likelihood function.

The calculation of the prior probability value is based on the probability density image converted from the similarity measurement image; the region corresponding to the maximum value of the cross-correlation matching is the region with the greatest similarity; the probability value should be greater than or equal to zero, so all the values of similarity measurement are positive; the values of the similarity measurement are normalized to obtain.

The posterior probability is calculated as follows:

$$Pr(U_x | U_{N_x}) = \frac{Pr(U_{N_x} | U_x) Pr(U_x)}{Pr(U_{N_x})}. \quad (1)$$

In the formula, $Pr(U_x)$ is the prior probability, $U_x$ is the displacement of the matching block at xy position, $Pr(U_{N_x}/U_x)$ is the likelihood function, where $U_{N_x}$ is the displacement of the adjacent matching block (in the two-dimensional ultrasonic motion displacement estimation, the adjacent matching block is selected as the four neighborhoods (two vertical directions and two horizontal directions) of the currently estimated block); $U_{N_x}$ is $\{Ux':X'\in N_x\}$;

$$Pr(U_{N_x} | U_x) = \prod_{x' \in N_x} Pr(U_{x'} | U_x); \quad (2)$$

$$Pr(U_{x'} | U_x) \propto \max_{V_{x'}} \left[ Pr(V_{x'}) \exp\left( \frac{-\|V_{x'} - U_x\|^2}{2\sigma_u^2} \right) \right]. \quad (3)$$

In the formula: x represents a position of the current matching block, $U_x$ presents a displacement of the current matching block at the position x, and $Pr(U_x)$ is a prior probability value of $U_x$; x' represents positions of four neighboring matching blocks adjacent to the current matching block, $U_{x'}$ represents a displacement of one of the four neighboring matching blocks, $\{Ux':X'\in N_x\}$; $V_{x'}$ represents a candidate displacement of one of the four neighboring matching blocks, and $Pr(V_{x'})$ is a prior probability value of $V_{x'}$; $U_{N_x}$ represents the displacements of the four neighboring matching blocks, and $Pr(U_{N_x})$ represents a prior probability value of $U_{N_x}$; $Pr(U_{N_x}/U_x)$ is the likelihood function; $Pr(U_{x'}|U_x)$ is the probability value that when the displacement of the current matching block at xposition is $U_x$ and the displacement of the neighboring matching block at x'position is $U_{x'}$; $\|V_{x'}-U_x\|^2$ is a distance between these two points x and x', where a value of $\sigma_u$ is taken as empirical value. The result of formula (2) can be obtained by the calculation of Formula (3).

$$MPPS = \Sigma^{m=1}_{m=-1} \Sigma^{n=1}_{n=-1} \max Pr(u+m, v+n) \ m=0 \text{ or } n=0 \quad (4)$$

In the formula, u and v are the positions of the candidate points, and Pr is the posterior probability value of the point. The formula execution condition (M=0 or n=0) restricts the accumulation process to be the central candidate point and its four neighborhoods.

Step S14: Determine the seed point. The basis for the seed point judgment is whether the sum of the maximum posterior probability of the candidate point and the neighboring point is greater than the set threshold and whether the maximum absolute displacement difference is less than the set threshold.

Step S20: Perform guided search and displacement estimation:

Step S21: Determine an initial known-displacement point set, an interior point (IP) set and a boundary point (BP) set after the selection of seed point.

Figure 2:
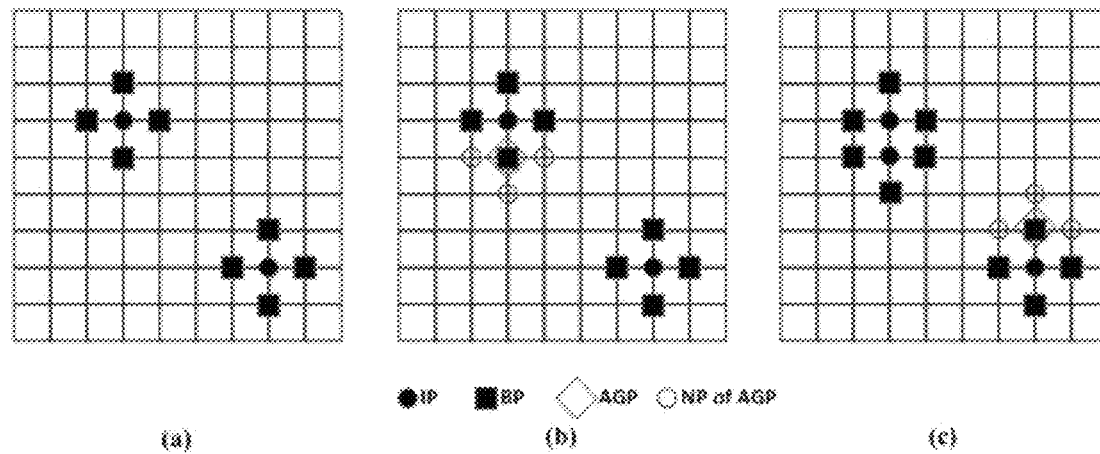
FIG. 2 is a schematic diagram of region-growing.

The black circle in FIG. 2 represents the interior point (IP) set, and the black square represents the boundary (BP) point set. The IP set and the BP set are combined to form a known-displacement point set. The red diamond-shaped AGP represents the active growing point of the selected region, and the black circle represents the neighborhood point of the AGP.

Step S22: Determine the active growing point; specifically select the point with the largest posterior probability value as the active growing point in the boundary point set in the determined known-displacement point set.

Step S23: Conduct guided search according to the displacement of the active growing point; perform the displacement estimation of region-growing near the active growing point, that is, in the four neighborhoods of the active growing point. In FIG. 2, the hollow circle represents the neighborhood points of the active growing point.

The determination and update of the displacement value corresponding to the neighborhood point in the region-growing Bayesian algorithm based on joint local polynomial fitting can be divided into the following three cases:

Case 1: If the neighborhood point of the current active growing point is an interior point, no estimation will be made, because the displacement of the interior point set determined by the Bayesian parameter is reliable; therefore, the displacement value of the interior point will not change with the progress of the guided search algorithm. The upper neighborhood of the active growing point marked in FIG. 1 represents the situation where the neighborhood point is an interior point.

Case 2: If the neighborhood point of the current active growing point is a boundary point, its displacement value is estimated in the previous step, but the displacement of the point in the boundary point set should be re-estimated according the search range determined by the current active growing point. The update of the boundary point displacement values will be divided into the following two cases. If the maximum posterior probability value estimated according to the range determined by the current active growing point is greater than the previously determined maximum posterior probability value of the neighborhood point, the absolute difference is judged between the displacement value obtained by matching the current neighborhood points and the displacement value of the active growing point. If the absolute displacement difference is less than the set threshold, replace the displacement value of the neighborhood point with the newly obtained displacement value. If the absolute displacement difference is greater than the set threshold, perform the local polynomial fitting in Step 3 and adjust the displacement result according to the fitted value of the displacement. If the maximum posterior probability value of the boundary point obtained by the current active growing point estimation is less than the previously determined maximum posterior probability value of the neighborhood point, the displacement value of the current boundary point will not change.

Case 3: If the neighborhood point of the current active growing point is an unknown-displacement point, its displacement value has not been estimated. The displacement of the unknown-displacement point will be estimated according to the range guided by the active growing point. As with the boundary point, the displacement value is updated by judging the absolute difference between the estimated displacement value of the neighborhood point and the displacement value of the active growing point; if the absolute displacement difference is less than the set threshold, the displacement value of the neighborhood point will be replaced by the newly obtained displacement value; if greater than the set threshold, perform the step of local polynomial fitting mentioned in Step 3.

Step S30: Conduct local polynomial fitting:

Step S31: The step of local polynomial fitting is to obtain the fitted value by fitting the displacement of the point to be estimated according to the displacement of the known-displacement interior point set around the estimated point (within a range of 2 pixel points at the upper, lower, right and right with the point to be estimated as the center); when the error of the fitted value is less than the error of the estimated value, the fitted value will displace the estimated displacement value of the neighborhood.

The local polynomial fitting formula is as follows:

$$f(x, y) = a_0 + a_1 x^2 + a_2 y^2 + a_3 xy + a_4 x + a_5 y; \tag{5}$$

$$R^2 = \sum_{i=1}^{N} [g(x, y) - (a_0 + a_1 x^2 + a_2 y^2 + a_3 xy + a_4 x + a_5 y)]^2. \tag{6}$$

In the formula, (x, y) are coordinates of one displacement point; N represents a total number of displacement points used for calculating the local polynomial fitting formula; $a_0$, $a_1$, $a_2$, $a_3$, $a_4$, $a_5$ are coefficients of the local polynomial fitting formula to be solved; i represent a serial number; g(x,y) is a known displacement, and $R^2$ is a sum of squared errors; wherein N estimated neighboring displacement points are selected, assuming that a distribution of these N estimated neighboring displacement points satisfies the formula (5); a least square method is adopted to solve the coefficients $a_0$, $a_1$, $a_2$, $a_3$, $a_4$, $a_5$, and then the formula (6) is obtained. To solve the coefficient ai ($0 \le i \le 5$) in f(x,y), it is necessary to minimize the sum of squared errors. The calculation method is to take the partial derivative of the sum of squared errors and make the partial derivative equal to zero; convert the equation to a matrix, as follows:

$$\begin{bmatrix} \frac{1}{N}\sum_{i=1}^{N} x^4 & \frac{1}{N}\sum_{i=1}^{N} x^2 y^2 & \frac{1}{N}\sum_{i=1}^{N} x^3 y & \frac{1}{N}\sum_{i=1}^{N} x^3 & \frac{1}{N}\sum_{i=1}^{N} x^2 y & \frac{1}{N}\sum_{i=1}^{N} x^2 \\ \frac{1}{N}\sum_{i=1}^{N} x^2 y^2 & \frac{1}{N}\sum_{i=1}^{N} y^4 & \frac{1}{N}\sum_{i=1}^{N} xy^3 & \frac{1}{N}\sum_{i=1}^{N} xy^2 & \frac{1}{N}\sum_{i=1}^{N} y^3 & \frac{1}{N}\sum_{i=1}^{N} y^2 \\ \frac{1}{N}\sum_{i=1}^{N} x^3 y & \frac{1}{N}\sum_{i=1}^{N} xy^3 & \frac{1}{N}\sum_{i=1}^{N} x^2 y^2 & \frac{1}{N}\sum_{i=1}^{N} x^2 y & \frac{1}{N}\sum_{i=1}^{N} xy^2 & \frac{1}{N}\sum_{i=1}^{N} xy \\ \frac{1}{N}\sum_{i=1}^{N} x^3 & \frac{1}{N}\sum_{i=1}^{N} xy^2 & \frac{1}{N}\sum_{i=1}^{N} x^2 y & \frac{1}{N}\sum_{i=1}^{N} x^2 & \frac{1}{N}\sum_{i=1}^{N} xy & \frac{1}{N}\sum_{i=1}^{N} x \\ \frac{1}{N}\sum_{i=1}^{N} x^2 y & \frac{1}{N}\sum_{i=1}^{N} y^3 & \frac{1}{N}\sum_{i=1}^{N} xy^2 & \frac{1}{N}\sum_{i=1}^{N} xy & \frac{1}{N}\sum_{i=1}^{N} y^2 & \frac{1}{N}\sum_{i=1}^{N} y \\ \frac{1}{N}\sum_{i=1}^{N} x^2 & \frac{1}{N}\sum_{i=1}^{N} y^2 & \frac{1}{N}\sum_{i=1}^{N} xy & \frac{1}{N}\sum_{i=1}^{N} x & \frac{1}{N}\sum_{i=1}^{N} y & 1 \end{bmatrix} \begin{bmatrix} a_1 \\ a_2 \\ a_3 \\ a_4 \\ a_5 \\ a_0 \end{bmatrix} = \begin{bmatrix} \frac{1}{N}\sum_{i=1}^{N} f(x,y)x^2 \\ \frac{1}{N}\sum_{i=1}^{N} f(x,y)y^2 \\ \frac{1}{N}\sum_{i=1}^{N} f(x,y)xy \\ \frac{1}{N}\sum_{i=1}^{N} f(x,y)x \\ \frac{1}{N}\sum_{i=1}^{N} f(x,y)x \\ \frac{1}{N}\sum_{i=1}^{N} f(x,y) \end{bmatrix}. \tag{7}$$

The matrix form in Formula (7) can be abbreviated as AX=B, A is a matrix with a size of 6×6, and the specific value is the leftmost value of the above equation. X is the column matrix $a_i$ formed by the unknown coefficients to be solved, where $0 \leq i \leq 5$ and the matrix size is 6×1. B is a column matrix with a size of 6×1, and its specific value is the rightmost value of the above equation. The problem of solving the coefficient $a_i$ ($0 \leq i \leq 5$) in the local polynomial fitting formula f(x,y) is transformed into the problem of solving the matrix equation, that is, solving AX=B.

The unknown parameters of the fitting equation can be obtained according to the matrix formula. The condition for local fitting in the algorithm is determined by the displacement difference, and local polynomial fitting is performed when the calculated displacement difference (the difference between the estimated displacement of the neighborhood point and the displacement of the active growing point) is greater than the set threshold. The step of local polynomial fitting is to obtain the fitted value by fitting the displacement of the point to be estimated according to the displacement of the known-displacement interior point set around the estimated point (within a range of 2 pixel points at the upper, lower, right and right with the point to be estimated as the center). According to the fitting formula, it can be found that the required parameter a0 is the displacement value of the point to be estimated. When the error of the fitted value is less than the error of the estimated value, the fitted value will replace the estimated displacement value of the neighborhood.

Step S32: Add new boundary point to the known-displacement point set after displacement estimation, convert the initial points with unknown displacement into points with known displacement in the neighborhood point set of active growing points, and update the BP set of the known-displacement point set to generate a new BP set; convert the active growing points from members of BP set to members of IP set, because the displacement values of all its neighborhoods (4 neighborhoods) have been estimated.

Step S33: Execute the algorithm until all members of the unknown-displacement point set are converted to the members of known-displacement point set.

Step S40, Update a status of the point to be estimated:

Step S41: Adding a new boundary point to the known-displacement point set after displacement estimation and fitting estimation.

Step S42: Converting initial unknown-displacement points into known-displacement points in the neighborhood point set of the active growing points, and updating the BP set of the known-displacement point set to generate a new BP set.

Step S43: Converting the active growing points from members of the BP set to members of the IP set after estimation, and repeating the above steps until all members of the unknown-displacement point set are converted to the members of known-displacement point set.

Step S50, strain elastogram calculation: the ultrasonic strain elastic image can be obtained by performing differential calculation on the ultrasonic elastic motion displacement field estimated by the two-dimensional joint local polynomial fitting region growth Bayesian algorithm.

The algorithm of the present invention and the traditional algorithm perform experiments on digital phantom data and in vivo ultrasound data with different compression ratios to calculate the contrast-to-noise ratio (CNR) value and modulus inversion. In the digital phantom experiment, compression from 1% to 5% and constant transverse shear (2%) deformation are applied to the Ω shaped digital phantom model. The experimental results show that the displacement image obtained by the algorithm of the invention is smoother than that obtained by the traditional algorithm, some noise points in the displacement image are removed, and the displacement calculation accuracy is improved.

The algorithm of the present invention is better in the capability to overcome signal decorrelation, and the strain elastogram generated by the displacement values calculated by the algorithm of the present invention is higher in the CNR value than that of strain elastogram obtained by the traditional algorithm, indicating that the algorithm of the present invention improves the accuracy of displacement estimation. In the in vivo ultrasound data experiment, there is fewer error in the axial displacement estimated by the algorithm of the present invention. The displacement diagram is smoother.

Compared with the axial strain elastogram obtained with the traditional algorithm, there is less visible "noise" in the axial strain elastogram obtained with the algorithm of the present invention. The CNR value of the strain elastogram is higher. Moreover, taking the displacement estimated by Bayesian inference as the input of the modulus inversion algorithm, we found that the small difference in the estimated displacement can be amplified during the modulus reconstruction. If the displacement estimated by Bayesian inference algorithm is used for modulus inversion, the reconstructed modulus distribution diagram will be better visualized. The experimental results of digital phantoms and in-vivo ultrasound data sets show that the introduction of Bayesian inference is effective in improving the quality of motion tracking.

FIGS. 3 to 10 are schematic diagrams of comparison between the method of the present invention and the traditional method. Observe the results in the axial displacement diagram and axial strain elastogram based on computer simulation data and in vivo data.

Figure 3:
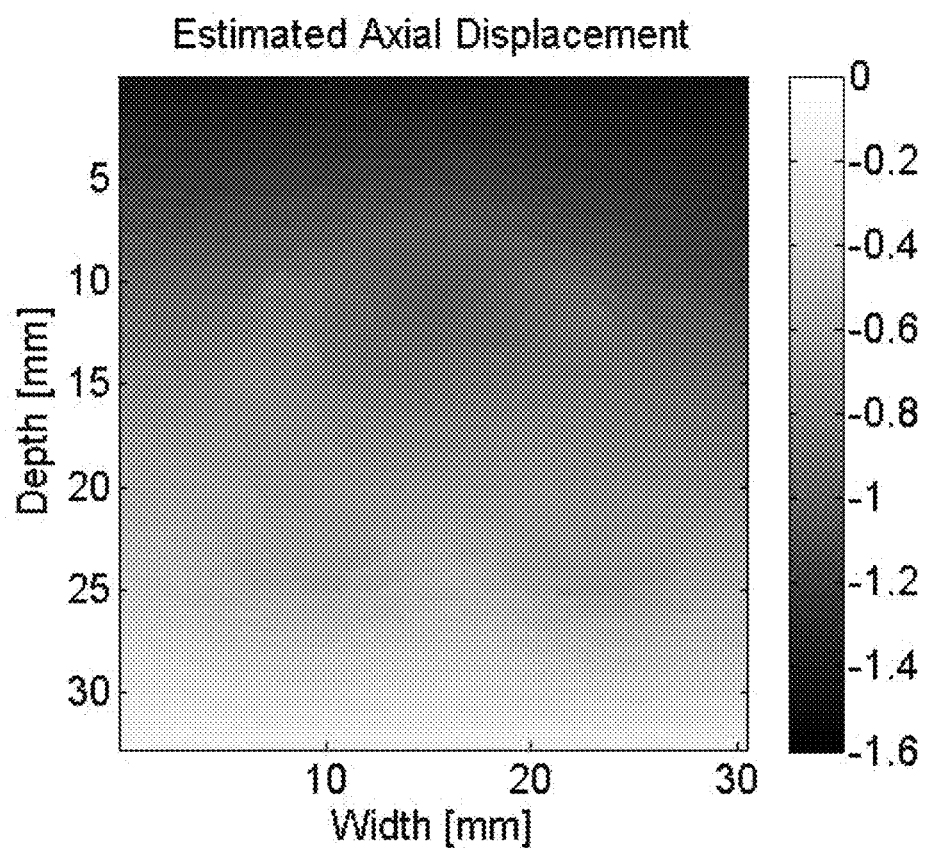
FIG. 3 is an axial displacement diagram of the traditional region-growing motion tracking algorithm based on computer simulation data.
Figure 4:
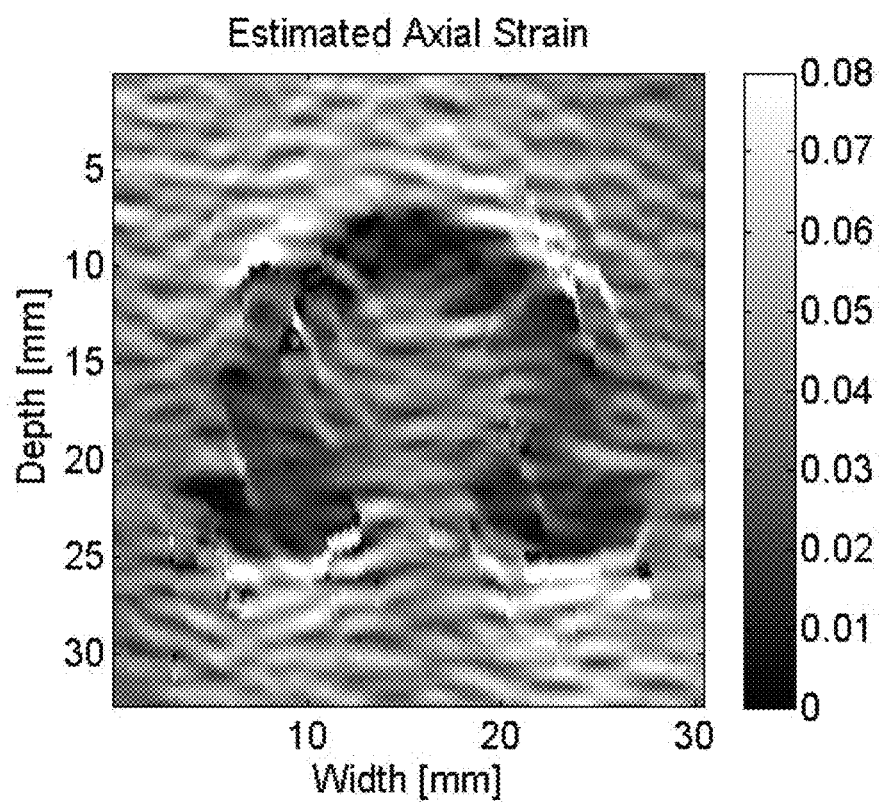
FIG. 4 is an axial strain elastogram of the traditional region-growing motion tracking algorithm based on computer simulation data.
Figure 5:
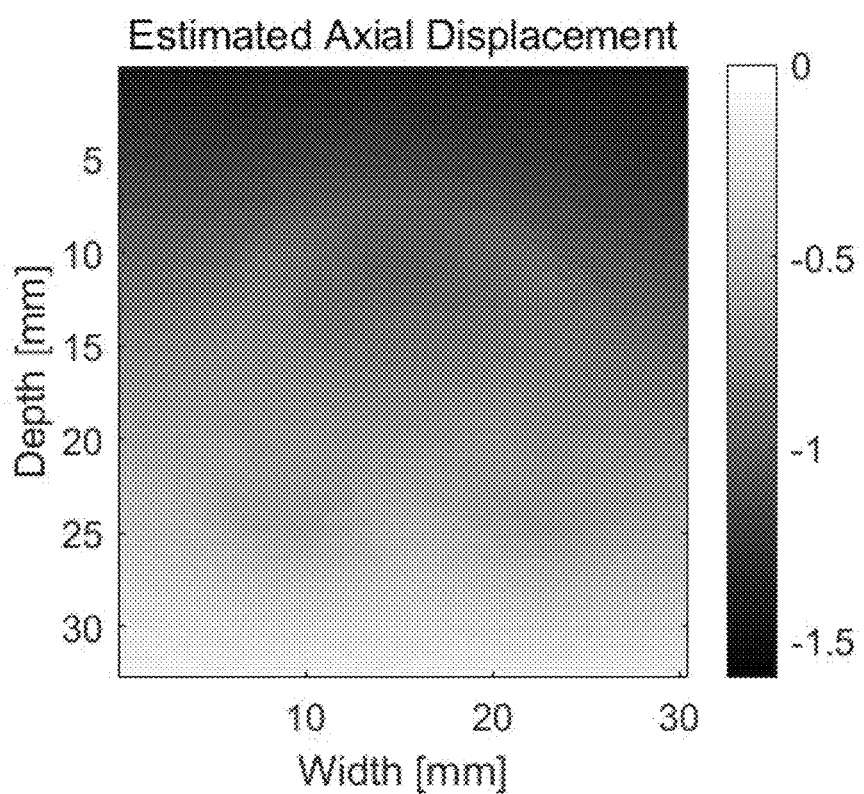
FIG. 5 is an axial displacement diagram of the method of the present invention based on computer simulation data.
Figure 6:
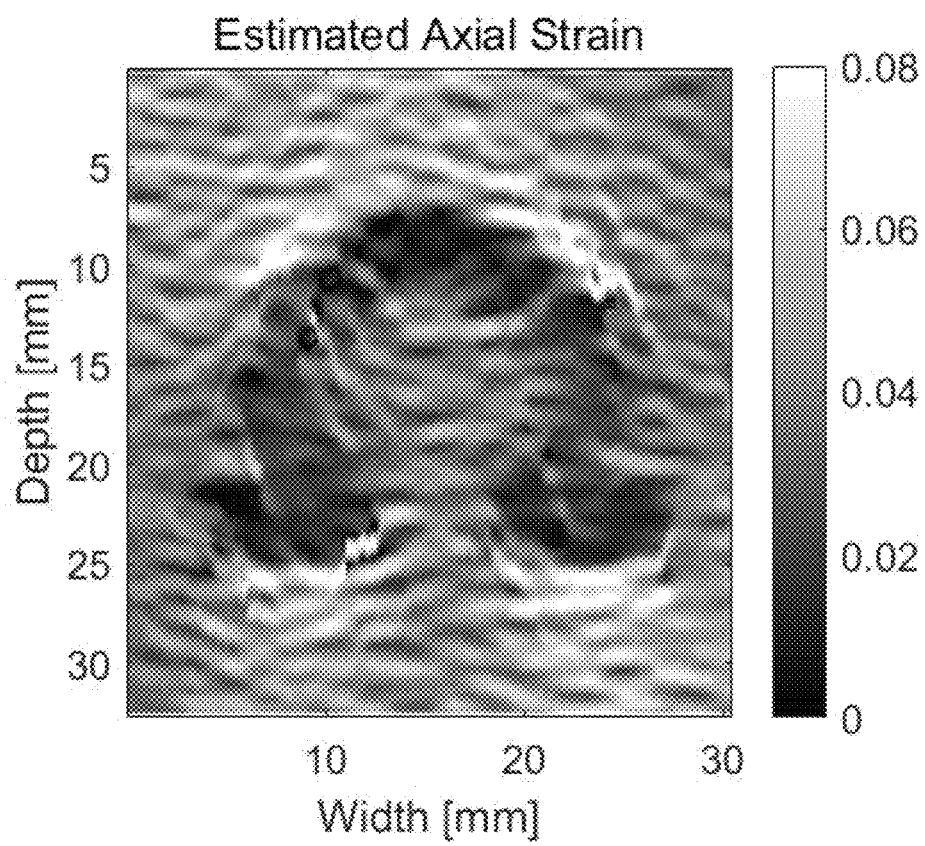
FIG. 6 is an axial strain elastogram of the method of the present invention based on computer simulation data.
Figure 7:
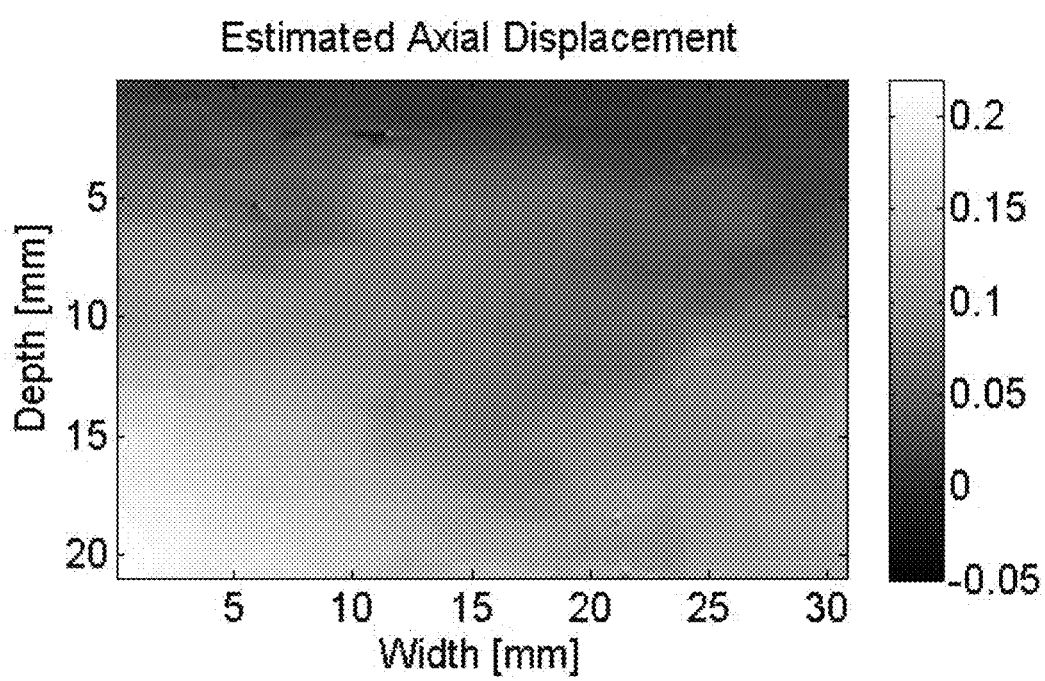
FIG. 7 is an axial displacement diagram of the traditional region-growing motion tracking algorithm based on in vivo ultrasound data.
Figure 8:
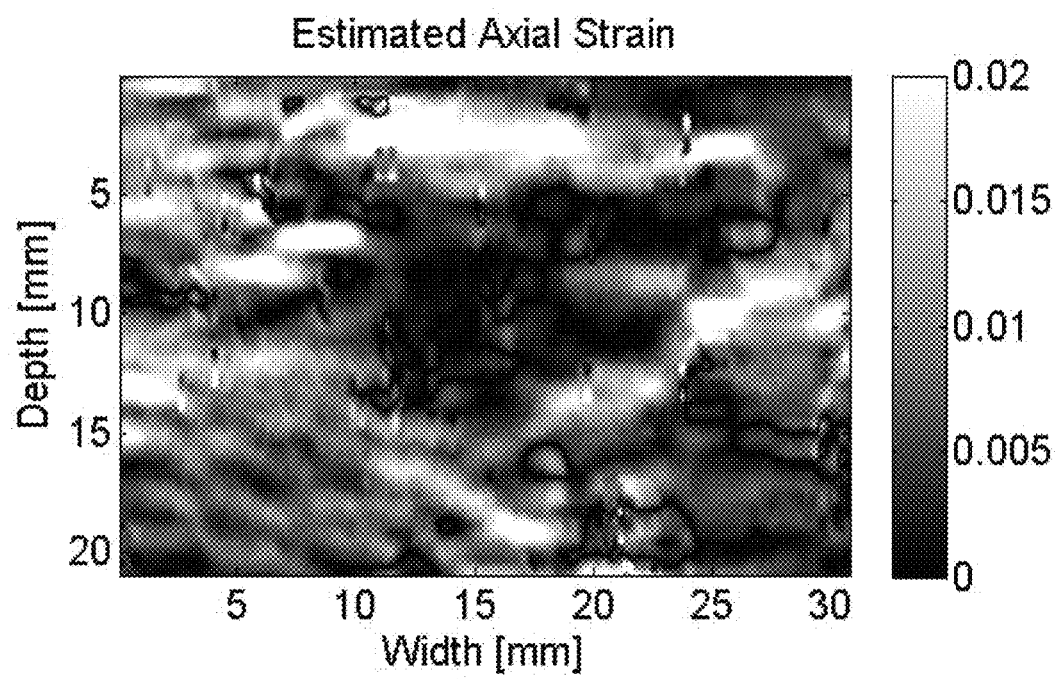
FIG. 8 is an axial strain elastogram of the traditional region-growing motion tracking algorithm based on in vivo ultrasound data.
Figure 9:
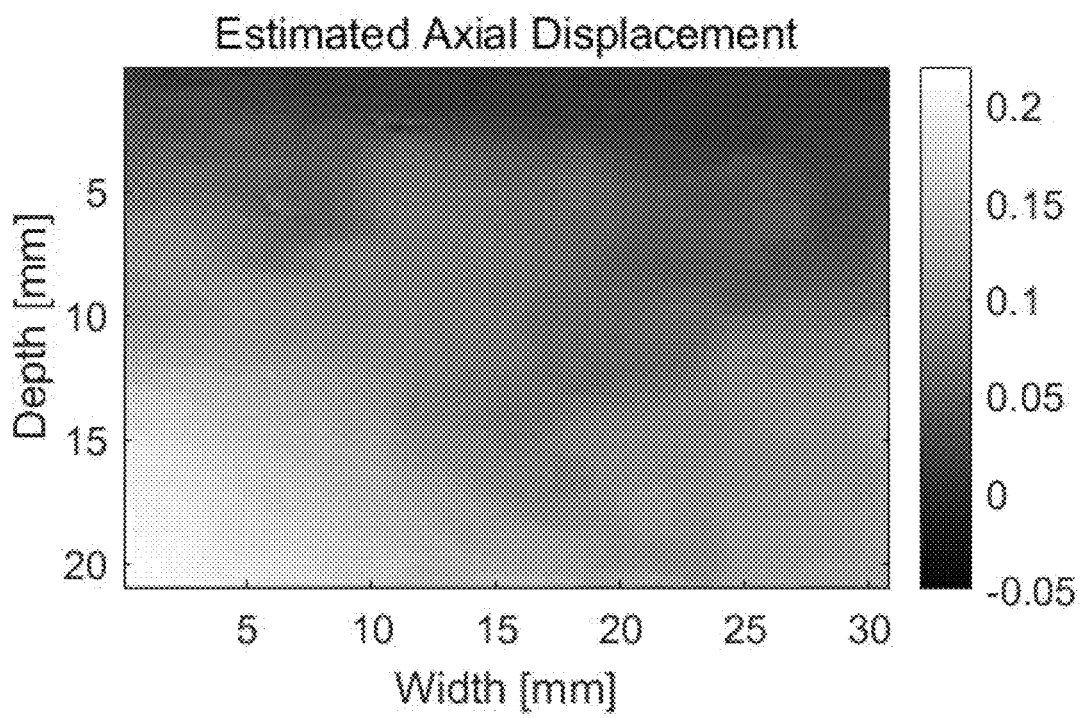
FIG. 9 is an axial displacement diagram of the method of the present invention based on in vivo ultrasound data.
Figure 10:
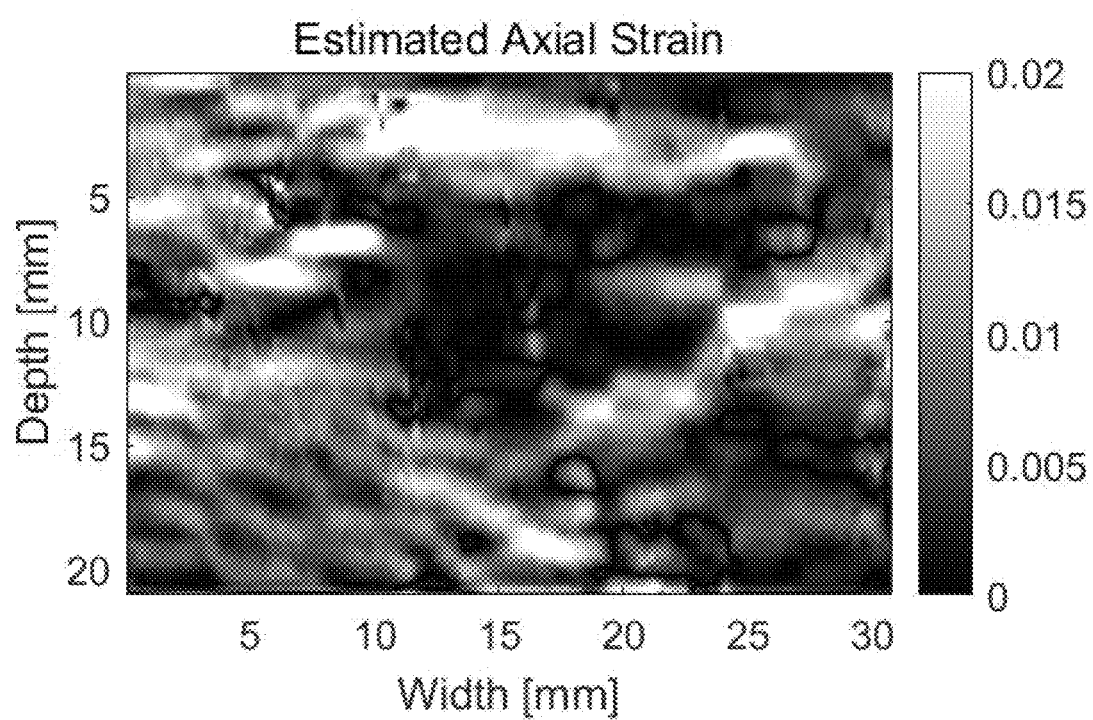
FIG. 10 is an axial strain elastogram of the method of the present invention based on in vivo ultrasound data.

FIGS. 5 and 6 are smoother than FIGS. 3 and 4. The algorithm of the present invention improves the accuracy of displacement estimation and the displacement tracking error is smaller than that of the conventional algorithm. Similarly, observe the results in the axial displacement diagram and the strain elastogram obtained in the experiment based on in vivo ultrasound data; the results obtained by the algorithm of the present invention are better.

Therefore, whether based on computer simulation data or in vivo ultrasound data, the algorithm of the present invention is effective for displacement estimation.

The above are not intended to limit the present invention in any form. Although the present invention has been disclosed as above with embodiments, it is not intended to limit the present invention. Those skilled in the art, within the scope of the technical solution of the present invention, can use the disclosed technical content to make a few changes or modify the equivalent embodiment with equivalent changes. Within the scope of the technical solution of the present invention, any simple modification, equivalent change and modification made to the above embodiments according to the technical essence of the present invention are still regarded as a part of the technical solution of the present invention.

What is claimed is:

1. A region-growing motion tracking method based on Bayesian inference and polynomial fitting, comprising the following steps:

Step 1: determining a seed point: selecting a region of interest (ROI), and then selecting a candidate point set from displacement estimation points in the ROI;

calculating posterior probability values of a candidate point in the candidate point set and four neighborhood points, a sum of maximum posterior probability values (MPPS) of these five points, and a maximum absolute displacement difference; judging whether the candidate point in the ROI is a seed point according to a set threshold, the MPPS and the maximum absolute displacement difference;

Step 2: performing guided search, displacement estimation: determining an initial known-displacement point set, an interior point (IP) set and a boundary point (BP) set after the selection of the seed point, selecting a point with the maximum posterior probability value as an active growing point within the determined BP set, then conducting guided search according to a displacement of the active growing point, and determining a neighborhood and a search range for displacement estimation according to a location and the displacement of the active growing point;

Step 3: conducting local polynomial fitting: when the displacement difference between the displacement estimation point and its neighborhood point is higher than the previously set threshold, the local polynomial fitting is carried out with the displacement estimation point as a center, and the local polynomial fitting is carried out using the IP point around the displacement estimation point, and a fitting value is taken as a new displacement estimation value;

Step 4: calculating strain elastogram: obtaining an ultrasonic strain elastic image through a differential calculation of displacement field of ultrasonic elastic motion.

2. The region-growing motion tracking method based on Bayesian inference and polynomial fitting according to claim 1, wherein the calculation of the posterior probability values is as follows:

A. calculating the prior probability values based on a block matching cross-correlation information;
B. calculating a likelihood function;
C. calculating the posterior probability values according to the prior probability values and the likelihood function;

$$Pr(U_x | U_{N_x}) = \frac{Pr(U_{N_x} | U_x)Pr(U_x)}{Pr(U_{N_x})};\qquad(1)$$

$$Pr(U_{N_x} | U_x) = \prod_{x' \in N_x} Pr(U_{x'} | U_x);\qquad(2)$$

$$Pr(U_{x'} | U_x) \propto \max_{V_{x'}}\left[Pr(V_{x'})\exp\left(\frac{-\|V_{x'} - U_x\|^2}{2\sigma_u^2}\right)\right];\qquad(3)$$

where, x represents a position of the current matching block, $U_x$ presents a displacement of the current matching block at the position x, and $Pr(U_x)$ is a prior probability value of $U_x$; x' represents positions of four neighboring matching blocks adjacent to the current matching block, $U_{x'}$ represents a displacement of one of the four neighboring matching blocks, $\{Ux':X' \in N_x\}$; $V_{x'}$ represents a candidate displacement of one of the four neighboring matching blocks, and $Pr(V_{x'})$ is a prior probability value of $V_{x'}$, $U_{N_x}$ represents the displacements of the four neighboring matching blocks, and $Pr(U_{N_x})$ represents a prior probability value of $U_{N_x}$; $Pr(U_{N_x}/U_x)$ is the likelihood function; $Pr(U_{x'}/U_x)$ is the probability value that when the displacement of the current matching block at xposition is $U_x$ and the displacement of the neighboring matching block at x'position is $U_{x'}$; $\|V_{x'}-U_x\|^2$ is a distance between these two points x and x', where a value of $\sigma_u$ taken as empirical value;

D. calculating the sum of the maximum posterior probability values (MPPS) according to the following formula;

$$MPPS = \Sigma^{m=1}_{m=-1}\Sigma^{n=1}_{n=-1}\max Pr(u+m, v+n)\ m=0\ \text{or}\ n=0\qquad(4)$$

where, u and v are the positions of the candidate points, Pr is the posterior probability value of the point, and a formula execution condition (M=0 or n=0) restricts the accumulation process to be a central candidate point and its four neighborhood points.

3. The region-growing motion tracking method based on Bayesian inference and polynomial fitting according to claim 2, wherein the block matching cross-correlation information of candidate point is obtained by a similarity measurement method.

4. The region-growing motion tracking method based on Bayesian inference and polynomial fitting according to claim 2, wherein the calculation of likelihood function is expressed by a probability density of the neighborhood points.

5. The region-growing motion tracking method based on Bayesian inference and polynomial fitting according to claim 2, wherein the calculation of the prior probability is as follows: a similarity measurement image is converted to a probability density image; a region corresponding to a maximum value of the cross-correlation matching is a greatest similarity region; the probability value is greater than or equal to zero, so all values of similarity measurement are positive; the values of the similarity measurement are normalized.

6. The region-growing motion tracking method based on Bayesian inference and polynomial fitting according to claim 1, wherein the seed point judgment step in Step 1 is: judging whether the sum of the maximum posterior probability of the candidate point and the four neighboring points is greater than the set threshold and whether the maximum absolute displacement difference is less than the set threshold.

7. The region-growing motion tracking method based on Bayesian inference and polynomial fitting according to claim 1, wherein the step of determining the initial known-displacement point set, IP set and BP set in Step 2 is as follows: all initial seeds are placed in a known-displacement point set, and the rest ROIs are the unknown-displacement point set; in the known-displacement point set, the points in the IP set are all points whose neighborhoods are in the known-displacement point set, and the rest known-displacement points are the boundary points.

8. The region-growing motion tracking method based on Bayesian inference and polynomial fitting according to claim 1, wherein the step of local polynomial fitting in Step 3 is as follows: the displacement of the point to be estimated is fitted according to the displacement of the known-displacement IP set around the point to be estimated, and then the fitted value is worked out; when an error of the fitted value is less than the error of the estimated value, the fitted value will displace the estimated displacement value of the neighborhood point.

9. The region-growing motion tracking method based on Bayesian inference and polynomial fitting according to claim 8, wherein the local polynomial fitting formula in Step 3 is as follows:

$$f(x, y) = a_0 + a_1 x^2 + a_2 y^2 + a_3 xy + a_4 x + a_5 y; \quad (5)$$

$$R^2 = \sum_{i=1}^{N} [g(x, y) - (a_0 + a_1 x^2 + a_2 y^2 + a_3 xy + a_4 x + a_5 y)]^2; \quad (6)$$

where, (x, y) are coordinates of one displacement point; N represents a total number of displacement points used for calculating the local polynomial fitting formula; $a_0$, $a_1$, $a_2$, $a_3$, $a_4$, $a_5$ are coefficients of the local polynomial fitting formula to be solved; i represent a serial number; g(x,y) is a known displacement, and $R^2$ is a sum of squared errors;

wherein N estimated neighboring displacement points are selected, assuming that a distribution of these N estimated neighboring displacement points satisfies the formula (5);

a least square method is adopted to solve the coefficients $a_0$, $a_1$, $a_2$, $a_3$, $a_4$, $a_5$, and then the formula (6) is obtained.

\* \* \* \* \*